United States Patent
Reynier

(10) Patent No.: US 12,142,377 B2
(45) Date of Patent: Nov. 12, 2024

(54) METHOD FOR DATA COMMUNICATION BETWEEN AN INFUSION STATION AND A FRONT-END COMPUTING DEVICE IN A HEALTHCARE ENVIRONMENT

(71) Applicant: Fresenius Vial SAS, Brézins (FR)

(72) Inventor: Christophe Reynier, Chirens (FR)

(73) Assignee: Fresenius Vial SAS, Brezins (FR)

( * ) Notice: Subject to any disclaimer, the term of this patent is extended or adjusted under 35 U.S.C. 154(b) by 184 days.

(21) Appl. No.: 17/606,659

(22) PCT Filed: Jul. 2, 2020

(86) PCT No.: PCT/EP2020/068700
§ 371 (c)(1),
(2) Date: Oct. 26, 2021

(87) PCT Pub. No.: WO2021/001491
PCT Pub. Date: Jan. 7, 2021

(65) Prior Publication Data
US 2022/0189629 A1    Jun. 16, 2022

(30) Foreign Application Priority Data

Jul. 3, 2019    (EP) .................................... 19305908

(51) Int. Cl.
*G16H 20/17*    (2018.01)
*G16H 40/67*    (2018.01)
(Continued)

(52) U.S. Cl.
CPC .............. *G16H 40/67* (2018.01); *G16H 20/17* (2018.01); *H04L 67/12* (2013.01); *H04L 69/18* (2013.01); *H04L 67/02* (2013.01)

(58) Field of Classification Search
CPC ......... G16H 40/67; G16H 20/17; H04L 67/12
See application file for complete search history.

(56) References Cited

U.S. PATENT DOCUMENTS 5,685,844 A * 11/1997 Marttila ................ A61M 5/172
604/65
11,057,409 B1 * 7/2021 Bisht ....................... H04L 43/04
(Continued)

FOREIGN PATENT DOCUMENTS

| KR | 2019-0048720 | 5/2019 |
| WO | WO2012/026922 | 3/2012 |
| WO | WO2014/131729 | 9/2014 |

OTHER PUBLICATIONS

International Search Report and Written Opinion, counterpart International Appl. No. PCT/EP2020/068700 (Oct. 2, 2020) (11 pages).
(Continued)

*Primary Examiner* — Vivek Srivastava
*Assistant Examiner* — Hien V Doan
(74) *Attorney, Agent, or Firm* — Cook Alex Ltd.

(57) ABSTRACT

In a method for data communication between an infusion station (1) and a front-end computing device (2) in a healthcare environment data is in an upstream direction (A1) and received in a downstream direction (A2), by at least one infusion station (1) for carrying out an infusion operation. In addition, data is in the upstream direction (A1) received and in the downstream direction (A2) transmitted by at least one front-end computing device (2). Herein, data in the upstream direction (A1) is received from and in the downstream direction (A2) is transmitted to the at least one infusion station (1) by a driver module (DP1-DP4), and data in the upstream direction (A1) is transmitted to and in the downstream direction (A2) is received from the at least one front-end computing device (2) by a virtual device module (VD1, VD2).

15 Claims, 5 Drawing Sheets

(51) Int. Cl.
*H04L 67/12* (2022.01)
*H04L 69/18* (2022.01)
H04L 67/02 (2022.01)

(56) References Cited

U.S. PATENT DOCUMENTS

| | | | | |
|---|---|---|---|---|
| 11,450,419 | B1* | 9/2022 | Esman | G06F 3/0482 |
| 2002/0143290 | A1* | 10/2002 | Bui | A61M 5/172 |
| | | | | 604/67 |
| 2011/0087756 | A1 | 4/2011 | Biondi et al. | |
| 2013/0151750 | A1 | 6/2013 | Kanigicherla et al. | |
| 2015/0370973 | A1* | 12/2015 | Jones | G16H 20/17 |
| | | | | 705/2 |
| 2018/0328612 | A1* | 11/2018 | Sinha | H04L 63/0442 |
| 2018/0338018 | A1 | 11/2018 | S et al. | |
| 2019/0109714 | A1 | 4/2019 | Clark et al. | |

OTHER PUBLICATIONS

Office Action and Search Report (with English-language translation), counterpart Chinese App. No. 202080045523.1 (Oct. 26, 2023) (16 pages).

Office Action (with English-language translation), counterpart Chinese App. No. 202080045523.1 (Jul. 23, 2024) (14 pages).

Search Report (with partial English-language translation), counterpart Chinese App. No. 202080045523.1 (Jul. 23, 2024) (1 page).

\* cited by examiner

METHOD FOR DATA COMMUNICATION BETWEEN AN INFUSION STATION AND A FRONT-END COMPUTING DEVICE IN A HEALTHCARE ENVIRONMENT

The present application is a U.S. National Stage of PCT International Patent Application No. PCT/EP2020/068700, filed Jul. 2, 2020, which claims priority to EP Application No. 19305908.6, filed Jul. 3, 2019, both of which are hereby incorporated herein by reference.

The invention relates to a method for data communication between an infusion station and a front-end computing device in a healthcare environment according to the preamble of claim 1 and to a system for data communication in a healthcare environment.

In a method of this kind, at least one infusion station for carrying out an infusion operation transmits, in an upstream direction, or receives, in a downstream direction, data. A front-end computing device receives, in the upstream direction, or transmits, in the downstream direction, data relating to the at least one infusion station.

Infusion station may for example be a standalone infusion pump, such as a volumetric (peristaltic) infusion pump or a syringe infusion pump. The infusion station may alternatively be an arrangement of multiple infusion pumps, such as infusion pumps stacked on a rack.

Generally, a user may wish to initiate a data communication with one or multiple infusion stations comprising one or multiple infusion pumps in order to for example monitor ongoing infusion operations or to program infusion pumps for carrying out infusion operations. For this, a user may access a front-end computing device, such as a computing device, for example in the shape of a PC, a laptop computer or a tablet computer, or a communication device such as mobile phone or the like connected to a communication network in order to receive data from a pump device or transmit data towards a pump device.

Conventionally, a direct data path between a front-end computing device and an infusion station is to be established, such direct data path being characterized by a data transfer using a defined protocol. Different pump devices herein may use different communication protocols, and in addition communication protocols used for a data transfer may also depend on a specific communication channel, such as for a wire-bound communication (e.g., Ethernet/LAN) or for a wireless communication (e.g., WiFi). Different protocols herein may define different data structures, such that the use of different protocols comes with the effect that data of different devices is presented differently in different structures and potentially with a different contents. Hence, if a user via a front-end computing device wishes to connect to an infusion station, it is to be made sure that the front-end computing device is enabled to communicate with the particular infusion station, possibly requiring an update of the front-end computing device in order to install a software application which allows for a communication using a particular communication protocol required by an infusion station.

As a large variety of different infusion stations having pump devices of different types (e.g., volumetric (peristaltic) infusion pumps or syringe infusion pumps), of different families (e.g., infusion pumps of one manufacturer, but of particular different brands), and of different manufacturers exists, it may be a cumbersome task to keep front-end computing devices for example within a healthcare environment such as a hospital updated such that they are enabled to communicate with the infusion stations placed throughout the healthcare environment.

In particular, if a new device shall be used within a hospital environment, a suitable software update potentially needs to be installed on every single front-end device which potentially shall communicate with the new device.

WO 2014/131729 A2 describes a system for providing drug library data to a medical device located within a healthcare environment, the system comprising a local network and at least one medical device for administering a drug to a patient, the at least one medical device being located in the healthcare environment and connected to the local network. Drug library data herein is transferred to the at least one medical device via a public communication network.

It is an object of the instant invention to provide a method for data communication between an infusion station and a front-end computing device and a system for data communication in a healthcare environment which allow to facilitate a data communication between one or multiple infusion stations and front-end computing devices, while making administration of devices within a healthcare environment easier.

This object is achieved by means of a method comprising the features of claim 1.

Herein, the method further comprises the following steps: at least one of in the upstream direction receiving data from and in the downstream direction transmitting data to the at least one infusion station by a driver module, and at least one of in the upstream direction transmitting data to and in the downstream direction receiving data from the at least one front-end computing device by a virtual device module. The driver module herein is configured to at least one of, in the upstream direction, process data received from the at least one infusion station to provide said data to the virtual device module and, in the downstream direction, process data received from the virtual device module to transmit said data to the at least one infusion station. Furthermore, the virtual device module includes a data model defining a plurality of data structures in which data relating to the at least one infusion device is stored.

The driver module and the virtual device module may for example be hosted on a server system, such as a back-end server within a healthcare environment, e.g., a hospital. The server system herein may comprise a single server unit or may be comprised of multiple distributed servers together making up the server system. The driver and the virtual device module herein may reside on the same physical server, or may be hosted on different, distributed servers.

By means of the driver and the virtual device module an intermediate layer in between infusion stations and front-end computing devices is introduced, the intermediate layer providing for a translation and abstraction in the communication of data in between the infusion stations and the front-end computing devices.

In particular, the driver module serves to provide for a communication with one or multiple infusion stations, wherein the infusion stations may comprise one or multiple different pump devices of different types employing different protocols for communicating data. A driver module in particular manages a connection to an infusion station, is enabled to communicate using a communication protocol required by a specific infusion station, and hence is enabled to process data received from an infusion station and for transmission towards said infusion station using a particular communication protocol associated with that infusion station.

A virtual device module in turn provides for a communication with one or multiple front-end computing devices such that the front-end computing devices always communicate with the virtual device module. This makes it possible to use a defined, common protocol or set of protocols for data communication between the virtual device module and any front-end computing device.

The virtual device module comprises a data model defining a plurality of data structures. Within the data model, data processed by the driver module is stored in defined, dedicated data structures, such that data received from one or multiple infusion devices is organized in a defined structure according to the data structures of the data model. Within the virtual device module data relating to one or multiple infusion devices hence is organized in a structure independent from communication protocols by means of which data is communicated in between one or multiple infusion devices and the driver module.

The organization of data relating to one or multiple infusion devices within the data model included in the virtual device module allows to communicate with one or multiple front-end computing devices using a common communication protocols. In particular, data can be communicated from the virtual device modules towards one or multiple front-end computing devices using a common communication protocol, which is independent from any communication protocol via which data is communicated between the infusion devices and the virtual device module.

Hence, the data communication in between front-end computing devices and the virtual device module is independent from any data communication in between infusion devices and the virtual device module (via one or multiple driver modules). By means of the virtual device module a generic data model is provided which allows for a data transfer in between the front-end computing devices and the virtual device module. Data may be exchanged in between the virtual device module and front-end computing devices using a common communication protocol, the data communication being independent from a data communication in between the driver module and a related infusion device (involving a specific communication protocol used for the data communication).

By introducing the intermediate layer comprised of one or multiple driver modules and one or multiple virtual device modules, an administration of devices within a healthcare environment to enable a communication between different devices is facilitated, in that no adaption of software components on front-end computing devices is required if for example a new infusion station implementing a specific communication protocol is added. The front-end computing devices communicate with one or multiple virtual device modules making use of a defined, common protocol or set of protocols defining a data exchange between the virtual device modules and the front-end computing devices, such communication not been affected by the adding of new infusion stations to the system.

Rather, if a new infusion station requiring a particular communication protocol is added to the system, only a suitable, new driver module must be installed e.g. on a back-end server, without having to modify the front-end computing devices for enabling a communication. The driver module herein enables a data exchange in between the infusion station and a corresponding virtual device module, the driver module providing for a processing of the data both in the upstream direction towards the virtual device module and in the downstream direction towards the infusion station.

In one embodiment, different drivers may communicate with different infusion stations using different first communication protocols. In particular, infusion stations of different kinds may exist, comprising for example pump devices of different types (e.g. volumetric infusion pumps or syringe infusion pumps) and belonging to different device families (e.g., Fresenius currently is offering pump devices in the so-called Agilia family and other pump devices for example for an enteral feeding in the so-called Amika family). In addition, one infusion station, being constituted of for example a standalone pump device or a stack of pumps combined for example on a rack, may communicate using different communication channels, such as a wireless communication channel using Wi-Fi or a wire-bound communication channel using for example an Ethernet connection. Herein, for each protocol that is being used by any infusion station, one driver may exist and may be installed for example on a server system, such that the driver module enables the communication between an infusion station making use of that protocol and a corresponding virtual device module, such that data may be exchanged between the infusion station and the virtual device module.

Hence, a first driver module may for example exist for a communication with an infusion station making use of a first communication channel, such as a wire-bound communication channel such as an Ethernet connection. Such driver module may enable for example a communication making use of an Ethernet protocol. A second driver module may exist for a communication with an infusion station making use of a second communication channel, such as a wireless communication channel, enabling a communication making use of a Wi-Fi (wireless LAN) protocol, a Bluetooth protocol, an NFC (Near Field Communication) protocol or the like. A third driver module may exist for an infusion station of a different type and for example belonging to a different device family. Overall, one driver module may be provided for each communication channel between an infusion station and a corresponding virtual device module making use of a particular communication protocol.

In one embodiment, the first communication protocol may be based on WiFi, HTTP, or Ethernet. Such protocol may be standardized. The WiFi protocol for example is standardized in the IEEE 802.11 standard. The Ethernet protocol is standardized in the IEEE 802.3 standard. In addition, based on standardized protocols, proprietary modifications implemented by a pump manufacturer may be employed, such that a protocol used by a particular infusion station may, in addition to the standardized protocol schematic, employ a proprietary scheme.

A second communication protocol used for communicating in between the virtual device module and one or multiple front-end computing devices may be different than the first communication protocol, or may be the same. For example, the second communication protocol may be based on AMQP or HTTP. Herein, a common communication protocol may be used for communication in between front-end computing devices and one or multiple virtual device modules, the common, second communication protocol being independent from any communication protocol that is being used for communication in between infusion devices and associated driver modules.

Whereas different driver modules exist for different infusion stations and use different communication protocols for communicating with different infusion stations, the communication between the virtual device module and the one or multiple front-end computing devices takes place using a common protocol scheme, such that all front-end computing devices communicate with a virtual device module making use of the same communication protocol or a set of communication protocols. Hence, if a driver module is modified or added, the communication between the front-end computing devices and a virtual device module is not affected.

In one embodiment, the virtual device module, as the second communication protocol, uses an upstream protocol in the upstream direction and a downstream protocol different than the upstream protocol in the downstream direction. Hence, different protocols are employed dependent on whether a communication takes place in the upstream direction or in the downstream direction.

Whereas the upstream protocol may be based for example on AMQP, the downstream protocol may for example be based on HTTP.

Such use of different protocols in the upstream direction and in the downstream direction is based on that the virtual device module shall, in one embodiment, store data received from one or multiple infusion stations or from one or multiple front-end communication devices in the data model making use of the data structures being defined by the data model. In particular, a virtual device module may store data relating to an identity of a pump device of an infusion station, a status of a pump device of an infusion station, and capabilities of a pump device of an infusion station in associated, predefined data structures. Hence, the virtual device module consolidates data relating to pump devices and stores the data in an organized fashion in a structured, generic data model, such that the virtual device module may be accessed by one or multiple front-end computing devices in order to obtain, modify or transfer information relating to a particular pump device or a particular infusion station comprising multiple pump devices.

The structure of the data model is herein, in one embodiment, independent from the virtual device module, different virtual device modules using the same generic data model having the same structure.

In the data model, data may be stored for example using XML (Extended Markup Language).

For communicating data in between a driver module and an associated virtual device module a protocol allowing for a buffering of data may be employed, in particular AMQP (AMQP stands for Advanced Message Queuing Protocol), AMQP being an open standard application layer protocol for message oriented middleware and allowing for a queuing of data messages.

In particular, the virtual device module may store information relating to an identity of a pump device, such as the pump device's family, the type of the pump device and a version of a hardware or a software currently installed on the pump device in the data model.

In addition or alternatively, the virtual device module may store in the data model information relating to the pump status such as the connectivity of the pump device, an infusion status of an ongoing infusion operation, a location of a pump device on a rack, and a location of the pump device in a healthcare environment such as a hospital. Information relating to the infusion status may include a drug of an infusion operation, a dosage, a dose rate, a time of infusion, a time remaining of an infusion, patient information and the like.

In addition or alternatively, the virtual device module may store in the data model information relating to capabilities of a pump device, wherein the capabilities may depend on a communication channel by means of which the pump device is connected to a communication network and hence is enabled to communicate with a corresponding driver module. In particular, the capabilities may include clinical functions which are available depending on a communication channel by which the pump device is connected. For example, if a pump device is connected by means of a wireless communication channel, only a subset of clinical functions may be available in comparison to other communication channels, such as wire-bound communication channels. Such clinical functions may for example relate to an auto-programming, an auto-documentation, a drug library configuration, a technical configuration, a firmware upload, and a device event log relating to a pump device. For example, a firmware upload may be available only for a wire-bound communication channel, but not if the pump device is connected via a wireless communication channel.

For predefined kinds of information herein predefined data structures may exist in the data model included in the virtual device module, such that information relating to an infusion device is stored in predefined data structures, independent from any communication protocol that is being used for communicating data in between the infusion devices and the associated driver modules.

In one embodiment, the driver module is implemented as a dynamic-link library (in short: dll) or a windows service. A dynamic-link library represents a shared library which may be employed by software applications. Such dynamic-link libraries allow in a modular fashion to provide executable programming code which may be commonly executed by different applications. Dynamic-link libraries having the file ending .dll are in particular employed in a window operating system environment.

In one embodiment, the virtual device module groups infusion devices of infusion stations belonging to a common device family. Herein, for each device family one virtual device module may be installed, such that one virtual device module per family exists. Within a virtual device module information relating to pump devices belonging to the same family, but potentially being of different type (for example volumetric infusion pumps and syringe infusion pumps) may be stored and accessed by front-end computing devices.

For a data communication in between a driver module and a corresponding virtual device module a common protocol such as AMQP may be employed, wherein each driver module communicates with a corresponding virtual device module making use of the same protocol. One virtual device module herein may communicate with different driver modules, namely one driver module for each protocol that a pump device of a device family is using.

The object is also achieved by means of a system for data communication in a healthcare environment, the system comprising: at least one infusion station for carrying out an infusion operation, the at least one infusion station being configured to at least one of in an upstream direction transmit and in a downstream direction receive data, and at least one front-end computing device being configured to at least one of in the upstream direction receive and in the downstream direction transmit data relating to the at least one infusion station. The system furthermore comprises a server system hosting a driver module and a virtual device module, the driver module being configured to at least one of in the upstream direction receive data from and in the downstream direction transmit data to the at least one infusion station, and the virtual device module being configured to at least one of in the upstream direction transmit data to and in the downstream direction receive data from the at least one front-end computing device. Herein, the driver module is configured to at least one of, in the upstream direction, process data received from the at least one infusion station to provide said data to the virtual device module and, in the downstream direction, process data received from the virtual device module to transmit said data to the at least one infusion station using said first communication protocol. The virtual device module includes a data model defining a plurality of data structures in which data relating to the at least one infusion device is stored.

The advantages and advantageous embodiments described above for the method equally apply also to the system, such that it in this respect shall be referred to the above.

The idea underlying the invention shall subsequently be described in more details with reference to the embodiments shown in the figures. Herein:

Figure 1:
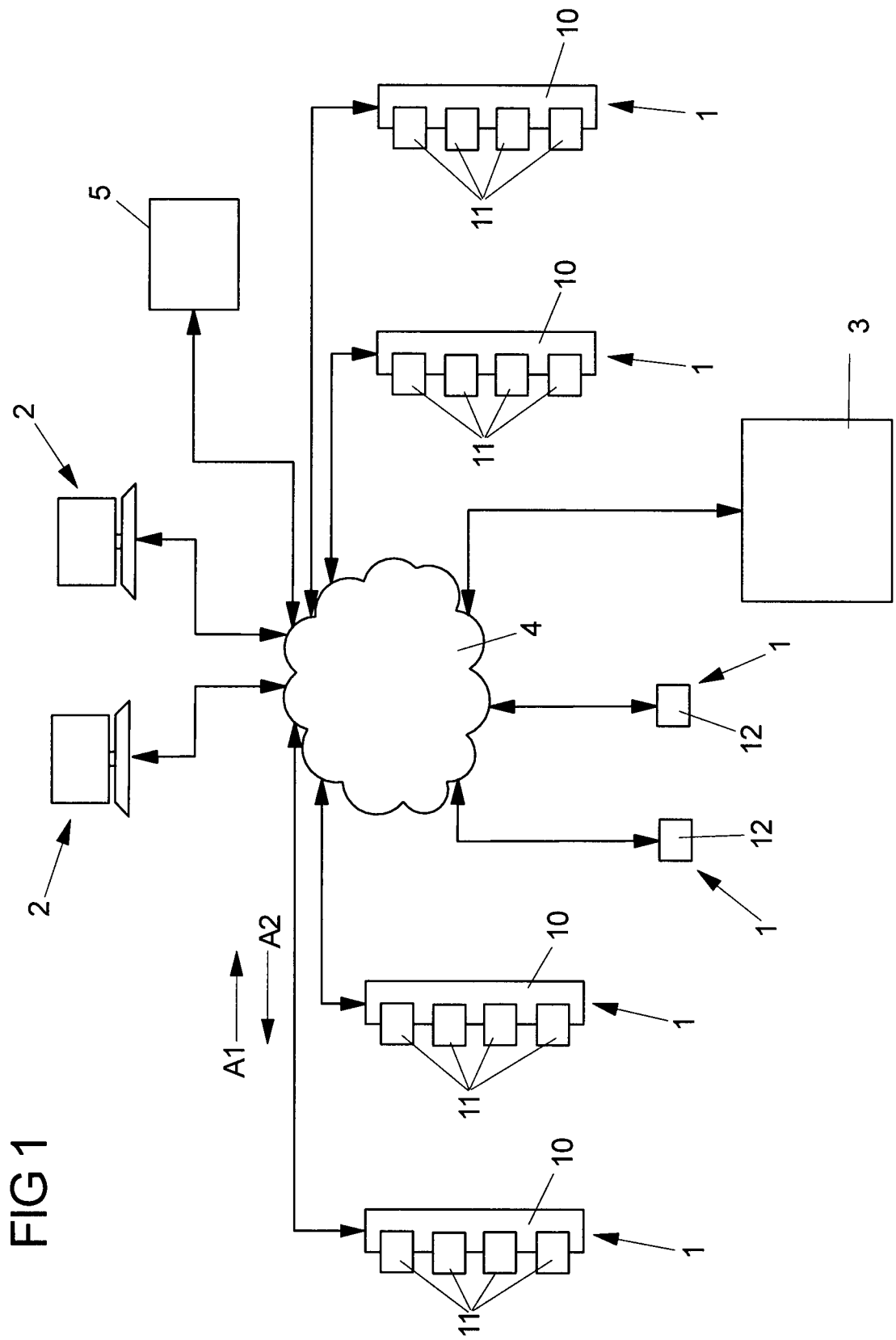
FIG. 1 shows a schematic drawing of a system for data communication in a healthcare environment.

FIG. 1 shows, in a schematic drawing, a setup as it may be found in a healthcare environment, such as a hospital. Namely, within a healthcare environment, infusion stations 1 such as stacks of pump devices 11 placed in an organized fashion on racks 10 or standalone pump devices 12 may be connected to a hospital communication network 4 and via the communication network 4 to a hospital information system (HIS). In addition, front-end computing devices 2 such as stationary personal computers (PC), laptop computers, tablet computers or mobile communication devices such as mobile phones are connected to the communication network 4. A server system 3, in particular a back-end server comprised of one or multiple (distributed) physical server entities, is connected to the communication network 4, the communication network 4 enabling a data exchange between the infusion stations 1, the front-end computing devices 2 and the server system 3.

In the context of a healthcare environment, users may wish to set up infusion operations to be carried out by one or multiple pump devices 11, 12, such pump devices 11, 12 being arranged throughout the healthcare environment in different wards and different rooms at the bedside of different patients. For this, a user may wish to transfer programming data to one or multiple pump devices 11, 12 in order to set up an infusion operation, or to manage and administer the configuration of one or multiple pump devices 11, 12, for example by transferring drug library data to one or multiple pump devices 11, 12, such drug library data providing general boundaries and guidelines for setting up infusion operations, such as boundaries for a dose rate for particular drugs and the like.

In addition, a user may wish to monitor an ongoing infusion operation carried out by one or multiple pump devices 11, 12, requiring a data transfer from pump devices 11, 12 towards front-end computing devices 2 via which a user can access the data.

Figure 2:
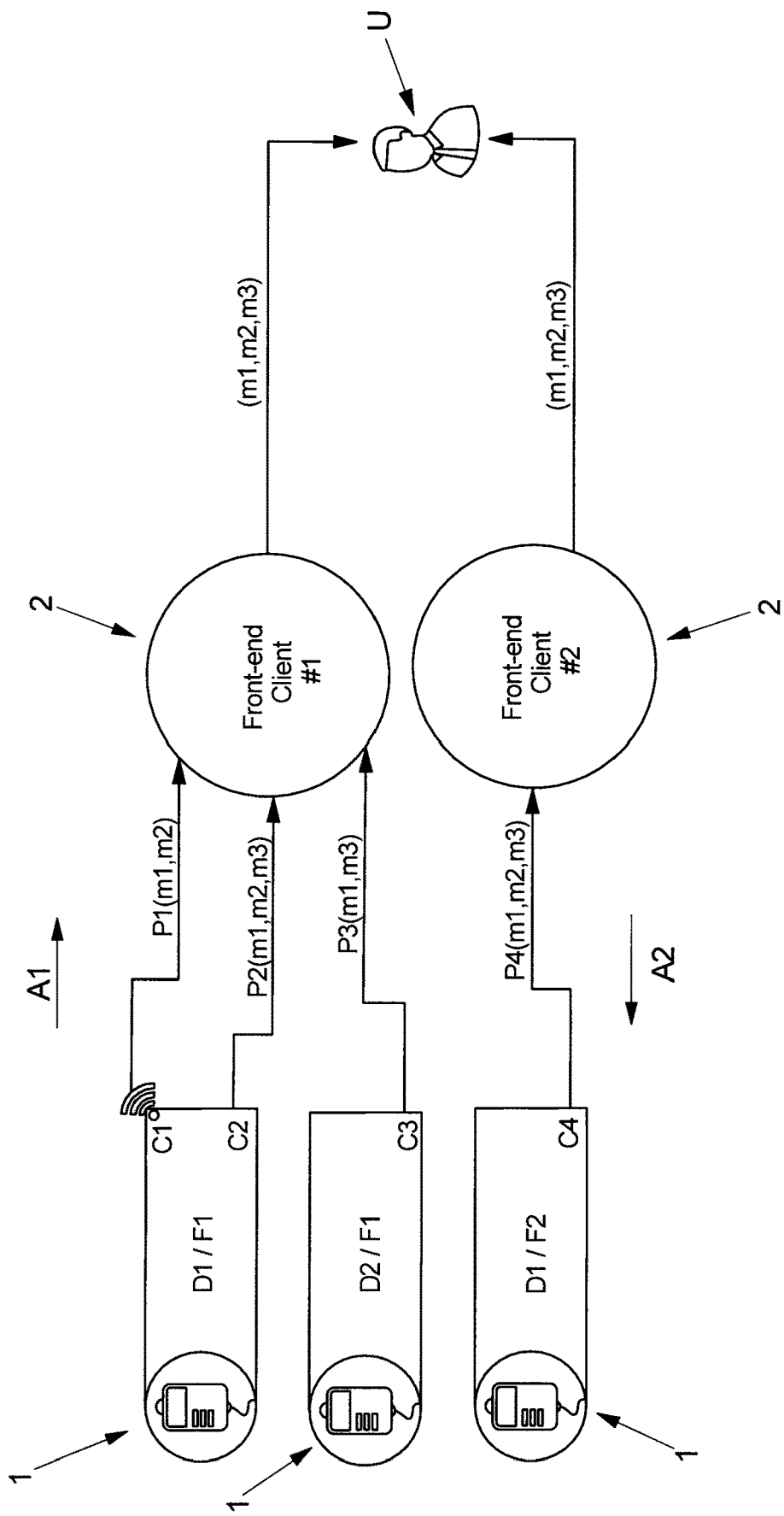
FIG. 2 shows a data communication between infusion stations and front-end computing devices employing a direct communication.

Referring now to FIG. 2, conventionally a data exchange between infusion stations 1—being comprised of multiple pump devices 11 placed on a rack 10 or of a standalone pump device 12, as schematically indicated in FIG. 1—and front-end computing devices 2 takes place by a direct data transfer via a communication channel C1-C4, each communication channel C1-C4 for example using a dedicated protocol P1-P4 for transmitting data for example in an upstream direction A1 from an infusion station 1 towards a front-end computing device 2, as this is illustrated in FIG. 2.

A first communication channel C1 herein may be a wireless channel, for example according to the Wi-Fi protocol and in addition using an HTTP protocol for the data transfer, for connecting an infusion station 1 having a pump device of a first type D1 and of a first family F1 to a front-end computing device 2. The same infusion station 1 herein may, alternatively or in addition, use a second communication channel C2, the second communication channel 2 for example being a wire-bound channel, such as an Ethernet channel adhering to the Ethernet protocol.

An infusion station 1 having a pump device of a different type D2, but of the same family F1, may use a third communication channel C3, for example also a wire-bound channel, but using a different protocol P3.

Another infusion station 1 having a pump device of type D1, but belonging to a different family F2, may use a communication channel C4, again using a different protocol P4 for communicating with a front-end computing device 2.

The pump type D1, D2 herein may indicate whether a pump device is a volumetric (peristaltic) infusion pump or a syringe infusion pump or another type of pump.

A device family F1, F2 may be defined by a certain manufacturer's brand, devices of the same family F1, F2 generally using a similar base architecture, for example a similar operating software.

Generally, dependent on what channel C1-C4 is used for transferring data, data messages m1-m3 are transferred according to the specifications of a specific protocol P1-P4, the protocol P1-P4 being used to pack the data messages m1-m3 according to the definitions of the protocol. In the upstream direction A1, herein, each front-end computing device 2 needs to understand the specific protocol P1-P4 which the infusion stations 1 use in order to unpack data messages m1-m3 for outputting data contained in such messages m1-m3 to a user wishing to access an infusion station 1, for example to monitor ongoing infusion operations. In a downstream direction A2 towards the infusion stations 1 data transfer takes place in an analogous fashion, each front-end computing device 2 using a specific protocol P1-P4 to transfer data towards an infusion station 1 via a specific communication channel C1-C4.

Hence, in the conventional setup of FIG. 2, each front-end computing device 2 needs to be enabled to communicate using specific protocols P1-P4 in order to be able to communicate with infusion stations 1. If an infusion station 1 using a pump device of a new type employing a different protocol shall be added to the system, this may require an updating of all front-end computing devices 2, which may be cumbersome and generally makes administration of the communication setup difficult.

Figure 3:
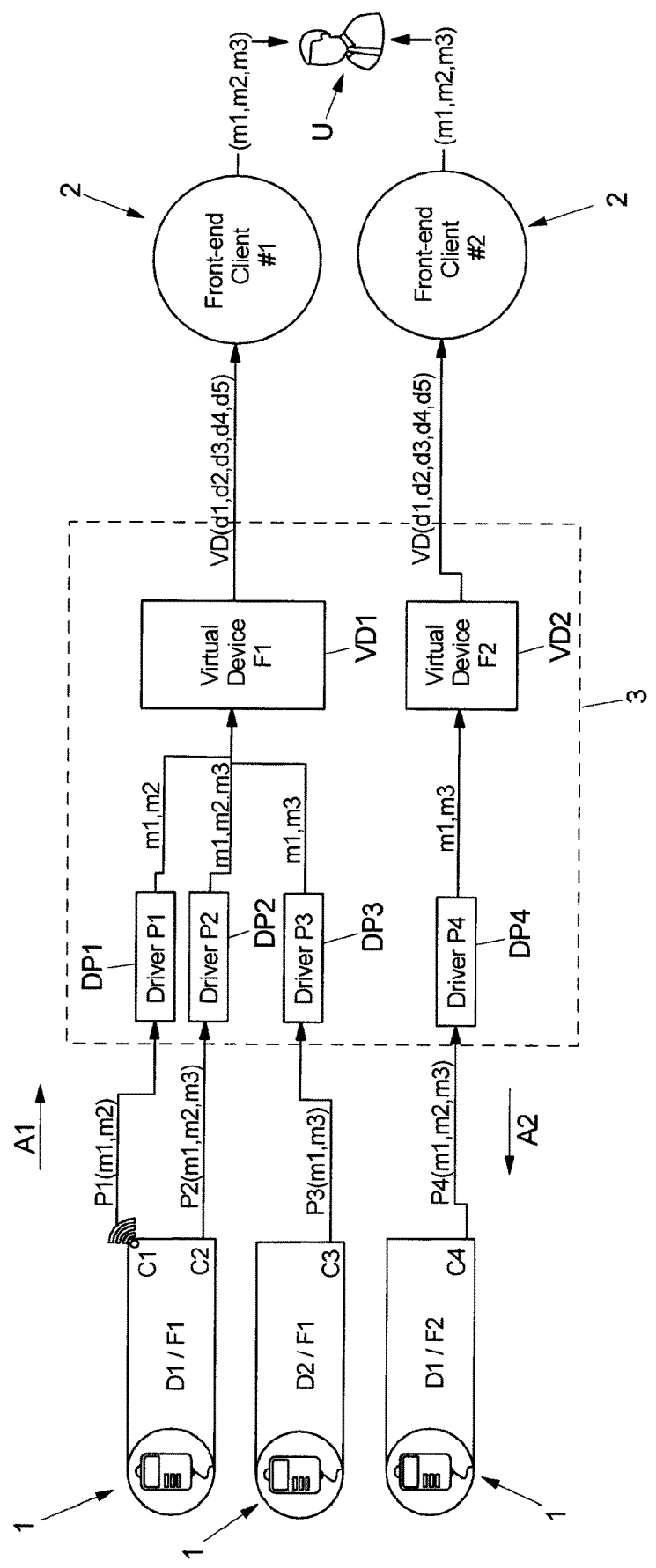
FIG. 3 shows a communication in between infusion stations and front-end computing devices employing an intermediate layer comprised of driver modules and virtual device modules for translating and abstracting a communication of data in between the infusion stations and the front-end computing devices.

Referring now to FIG. 3, it herein is proposed to introduce an intermediate layer in between infusion stations 1 and front-end computing devices 2, such intermediate layer for example being hosted on a server system 3, for example a back-end server being comprised of one or multiple (distributed) server entities within a healthcare environment.

The introduction of the intermediate layer generally is based on the idea to use a modular communication setup for providing a translation and abstraction in between infusion stations 1 and front-end computing devices 2. Both the infusion stations 1 and the front-end computing devices 2 herein shall communicate solely with the intermediate layer, such that a direct data transfer from infusion stations 1 towards front-end computing devices 2 and vice versa is no longer required, such that front-end computing devices 2 not necessarily must be enabled to communicate according to protocols P1-P4 being used by specific infusion stations 1 for specific communication channels C1-C4.

The intermediate layer is comprised of driver modules DP1-DP4 which serve to provide for a communication with the infusion stations 1. In addition, virtual device modules VD1, VD2 are installed, the virtual device modules VD1, VD2 being configured to provide for a data exchange with front-end computing devices 2.

The driver modules DP1-DP4 may for example be implemented by so-called dynamic-link libraries (.dll files), which e.g. within a Microsoft Windows operating system environment provide for dynamically linkable libraries of executable software code which may be employed by different software applications. Each communication channel C1-C4 using a specific protocol P1-P4 herein is associated with a specific driver module DP1-DP4, each driver module DP1-DP4 being enabled to provide for a communication using a specific protocol P1-P4.

Namely, in the example of FIG. 3, a first channel C1 using a first protocol P1, for example for a wireless data communication, exists associated with a first driver module DP1.

A second communication channel C2, for example a wire-bound channel using a second protocol P2, such as an Ethernet channel according to the Ethernet protocol, is associated with a second driver module DP2.

A third communication channel C3 using a third protocol P3 is associated with a third driver module DP3.

A fourth communication channel C4 using a fourth protocol P4 is associated with a fourth driver module DP4.

Each driver module DP1-DP4 is configured to provide for a data exchange via a specific, associated communication channel C1-C4 with an infusion station 1, the driver module DP1-DP4 managing the connection and being configured to process data for communication in the upstream direction A1 as well as in the downstream direction A2.

Namely, in the upstream direction A1 data which is being received via an associated communication channel C1-C4 is unpacked by removing a protocol framework used for transferring messages m1-m3. Such unpacked messages m1-m3 are then forwarded to an associated virtual device module VD1, VD2, as illustrated in FIG. 3. Within the virtual device modules VD1, VD2, as shall subsequently be explained in more detail, the data received from the driver modules DP1-DP4 is stored in a defined data model M (see FIG. 4), in which the data is organized in data structures M1, M10-M19.

In the downstream direction A2, in turn, each driver module DP1-DP4 is configured to process data messages m1-m3 received from an associated virtual device module VD1, VD2 to pack the data messages m1-m3 using the defined protocol framework of an associated protocol P1-P4, such that the data messages m1-m3 are forwarded to an infusion station 1 using that specific protocol P1-P4.

For communication in between the driver modules DP1-DP4 and the virtual device modules VD1, VD2 a common protocol, e.g., a protocol allowing for a queuing (buffering) of data messages, such as AMQP, may be employed.

Generally, data for transfer in the upstream direction A1 from infusion stations 1 towards the associated driver modules DP1-DP4 and virtual device modules VD1, VD2 may take place in a synchronous manner, the data transfer for example taking place in an event-triggered manner when data events occur, for example in the context of an infusion operation. The intermediate layer comprised of the driver modules DP1-DP4 and the virtual device modules VD1, VD2 herein is configured to buffer and store data received from the infusion stations 1, such that stored data may be forwarded to front-end computing devices 2 when they are requested by a user U.

The virtual device modules VD1, VD2 serve to communicate with front-end computing devices 2, the virtual device modules VD1, VD2 being accessible by the front-end computing devices 2 to provide a data transfer to and from the infusion stations 1. For each device family F1, F2, herein, one virtual device module VD1, VD2 may be implemented including a data model for the device family F1, F2. In the example of FIG. 3, a first device family F1 is associated with the virtual device module VD1. A second device family F2 is associated with the virtual device module VD2.

The virtual device modules VD1, VD2 in particular serve to store and consolidate information relating to infusion stations 1 and pump devices of such infusion stations 1 in a data model M.

In particular, within a virtual device module VD1, VD2 information relating to an identity of pumps of the associated device family F1, F2 may be stored, such information including information about the device family F1, F2, the pump type D1, D2, and a version of a pump device, such as a hardware version or an installed software version.

Alternatively or in addition, a virtual device module VD1, VD2 may store information relating to a pump status, such as a connectivity status, an infusion status, a location on a rack 10 of a pump device 11, a location of a pump device 11, 12 within a healthcare environment, such as a hospital, and the like. A connectivity status may include whether a pump device currently is connected to the communication network 4 or not, and—if yes—via which channel C1-C4. An infusion status may include whether an infusion operation is currently ongoing, and—if yes—which parameters are used for the infusion, such as a currently infused drug, a dose rate, an overall dosage, a time of infusion, and a time remaining for the infusion.

Alternatively or in addition, a virtual device module VD1, VD2 may store information relating to pump capabilities, wherein the capabilities may be different for different communication channels C1-C4 by means of which a specific infusion station 1 is connected to the communication network 4 and hence to the server system 3. For example, for a wireless communication channel C1 different capabilities may exist than for a wire-bound channel C2-C4. Such capabilities may relate to clinical functions and their availability, such clinical functions including for example an auto-programming function, an auto-documentation function, a drug library configuration function, a technical configuration function of a pump device, a firmware upload function, and a device event log function. For example, a firmware upload may only be possible if an infusion station is connected via a wire-bound communication channel C2-C4, but not via a wireless communication channel C1.

Figure 4:
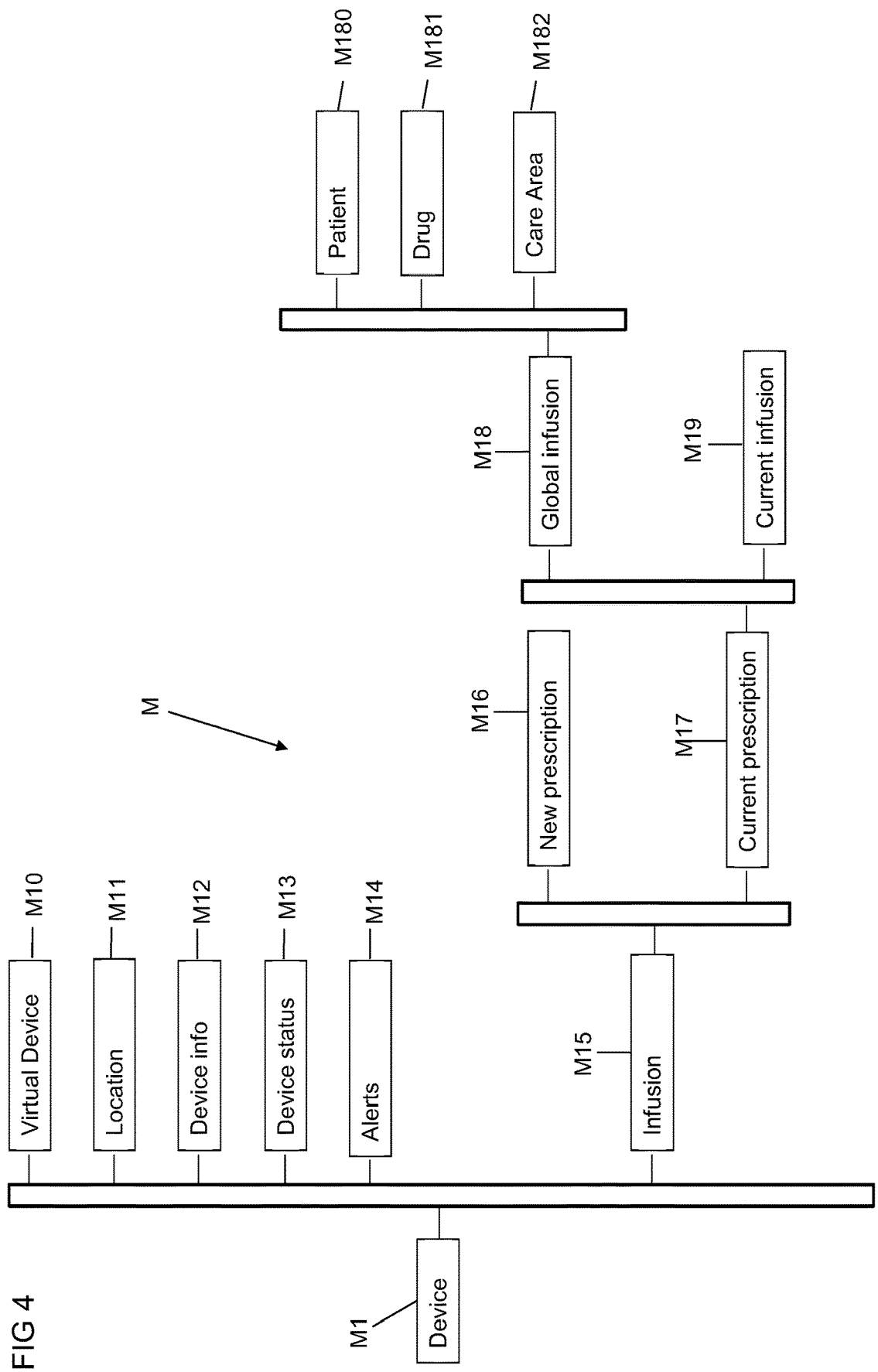
FIG. 4 shows a schematic view of a data model including data structures for storing data in an organized fashion in a virtual device module.

Referring now to FIG. 4, each virtual device module VD1, VD2 includes a data model M in which data relating to infusion stations 1 belonging to a device family F1, F2 associated with the virtual device module VD1, VD2 is stored in predefined, specific, dedicated data structures M1, M10-M19.

Herein, in the data model M for each infusion station 1 associated with a device family F1, F2 a data structure M1 exists including a tree of sub-structures. In the data structure M1 information relating to the particular infusion device is stored in dedicated structure elements.

In particular, in a first data structure M10 information relating to the virtual device module VD1, VD2 to which the infusion station 1 is associated may be stored.

In a second data structure M11 location information relating to the infusion station 1 may be stored, for example information identifying the exact physical location of the infusion station 1, such as information relating to a hospital, a ward, a room and a specific bed of a patient.

In a third data structure M12 information relating to the infusion station 1, such as information relating to a pump type, a pump family, a pump model and the like may be stored.

In a fourth data structure M13 information relating to a device status may be stored, relating for example to a status of an operating mode (for example "off", "standby", "booting", "on", "error", "maintenance"), a status of an infusion operation (for example "programming in progress", "installation in progress", "infusing", "stopped", "paused", "delayed infusion"), information relating to a battery status or the like may be stored.

In a fifth data structure M14 information relating to an alert may be stored, such as alarms and pre-alarms.

In a sixth data structure M15 information relating to a specific infusion may be stored. Herein, in a data sub-structure M16 information relating to a new prescription, and in a data sub-structure M17 information relating to a current prescription may be stored. In a substructure M18 relating to the data structure M17 herein global infusion information and current infusion information may be stored in data structures M18, M19. The data structure M18 relating to global infusion information herein may be associated with structure elements M180-M182 in which information relating to a patient (such as a patient's name, weight, height, gender and age), relating to a drug (such as a drug concentration and dilution) and relating to a care area (such as an intensive care unit) may be stored.

Figure 5:
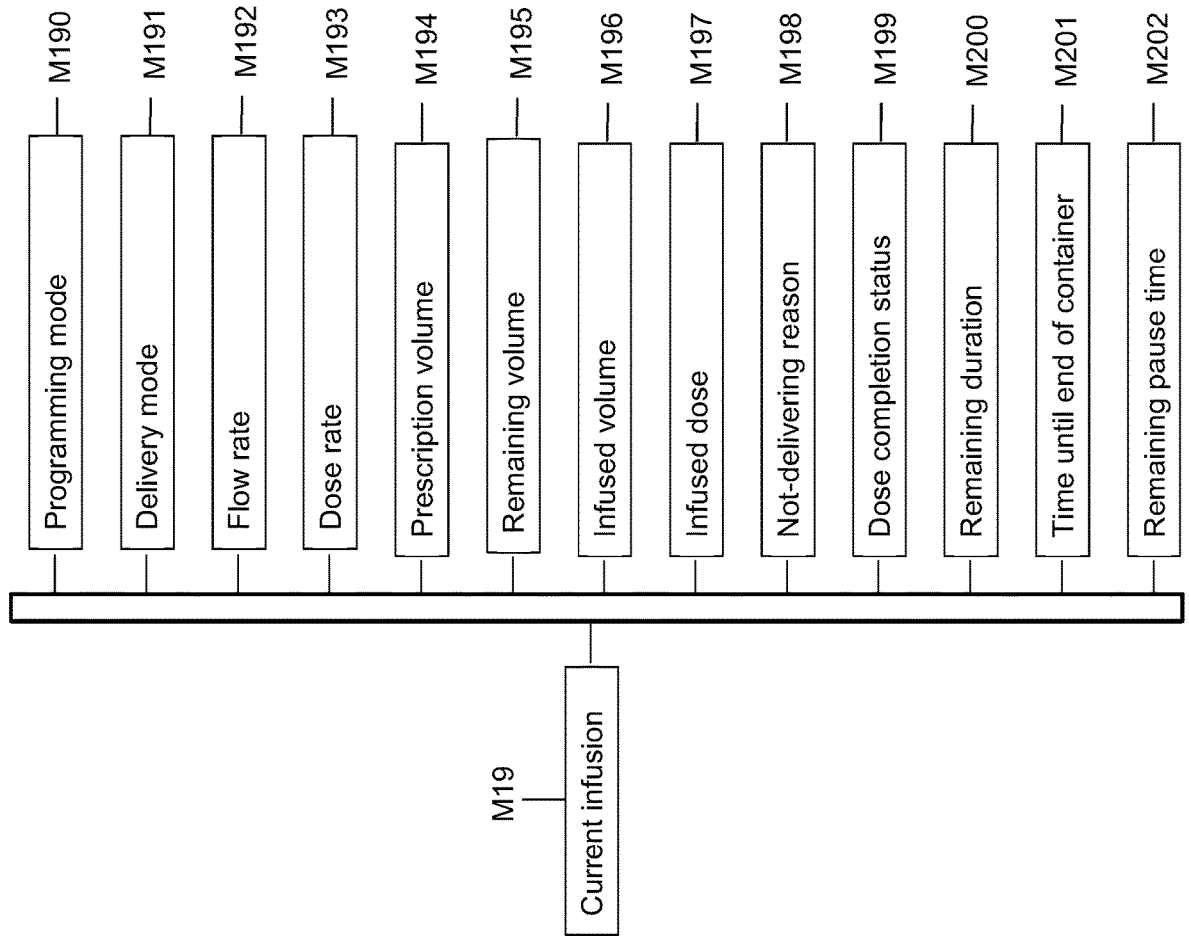
FIG. 5 shows a schematic view of a data structure including sub-structures.

In the sub-structure M19 (associated with the data structure M17 identifying information relating to a current prescription) information relating to a current infusion operation may be stored, as is illustrated in an illustrative example in FIG. 5.

In particular, within the data structure M19 all information relating to a currently ongoing infusion operation may be stored, such as information relating to a programming mode (data structure M190, for example "time rate", "volume rate", "volume time", "volume time rate", "TCI", "ramp", "sequence"), information relating to a delivery mode (data structure M191, for example "standard", "manual bolus", "programmed bolus", "simple bolus", "priming"), information relating to a flow rate (data structure M192), information relating to a dose rate (data structure M193), information relating to a prescription volume (data structure M194), information relating to a remaining volume (data structure M195), information relating to an infused volume (data structure M196), information relating to an infused does (data structure M197), information relating to reasons why a delivery has failed (data structure M198), information relating to a dose completion status (data structure M199), information relating to a remaining duration of the infusion operation (data structure M200), information relating to a time until an end of a container from which medication is drawn in the context of a sequential infusion operation (data structure M201), and information relating to a remaining pause time (data structure M202).

Within the data model M, hence, defined pieces of information are stored in defined data structures. The information is extracted from communication messages received from infusion stations, the processing of the communication messages taking place by the driver modules DP1-DP4, which forwards the data to the virtual device modules VD1, VD2 for storing in the generic data model M. Front-end computing devices 2 may then exchange data with the data model M, such that information may be provided to the front-end computing devices 2, and vice versa information issued by the front-end computing devices 2 may be stored in the data model M and transferred on to relating infusion stations 1.

Referring now again to FIG. 3, a virtual device module VD1, VD2 uses a common protocol or a set of protocols for communication with a front-end computing device 2, wherein such protocol or set of protocols is unaffected by protocols P1-P4 used for communication with the infusion stations 1.

For the communication between the virtual device modules VD1, VD2 and the front-end computing devices 2 herein different protocols may be used in the upstream direction A1 and in the downstream direction A2. In the upstream direction A1, for example, a queuing protocol, such as AMQP, may be used. In the downstream direction, in turn, an HTTP protocol, for example additionally employing XML and/or JSON, may be employed.

Generally herein, each virtual device module VD1, VD2 stores data d1-d5 extracted from messages m1-m3 received from infusion stations 1 (wherein each infusion station 1 may sent different messages containing different data) in for example a generic data model containing the pure data d1-d5. Such data is provided, if requested, to front-end computing devices 2 according to a defined protocol VD (illustrated by a data transfer VD(d1, d2, d3, d4, d5) in FIG. 3). In the downstream direction A2, data transfer takes place in an analogous fashion, wherein a different protocol may be employed for the data exchange.

Similarly as for the data transfer from the infusion stations 1 towards the virtual device modules VD1, VD2, a data transfer from the computing devices 2 towards the virtual device modules VD1, VD2 may take place in a synchronous, event-driven manner, for example in case a user U inputs information for example for programming an infusion station 1 and setting up an infusion operation. The virtual device modules VD1, VD2 stores such information in the data model M, such that the information is transferred to one or multiple infusion stations 1 in a buffered manner for example once a communication becomes possible, for example once an infusion station 1 is connected to the communication network 4 by means of a specific communication channel C1-C4.

By adding an intermediate layer in between infusion stations 1 and front-end computing devices 2, the intermediate layer being comprised of driver modules DP1-DP4 and virtual device modules VD1, VD2, an abstraction in between infusion stations 1 and front-end computing devices 2 is established. In the upstream direction A1, herein, by means of the intermediate layer a specific protocol schematic used for data transfer from an infusion station 1 by means of a specific communication channel C1-C4 is removed in the intermediate layer, and data is processed and consolidated into a generic data model M, which is buffered in an associated virtual device module VD1, VD2. Each front-end computing device 2 has to implement only a single virtual device protocol or set of protocols for communication with an associated virtual device module VD1, VD2 in order to access data from or send data towards an infusion station 1.

This bears the advantage that administration of the system becomes easy, as an addition or a modification of an infusion station 1 does not require a modification of front-end computing devices 2. If a new device is added to the system, in principle only a new driver module, for example in the shape of a dynamic-link library, needs to be installed and dynamically linked to a virtual device module VD1, VD2.

The idea underlying the invention is not limited to the embodiments described above, but may be implemented in an entirely different fashion.

Infusion stations may comprise one or multiple pump devices placed on a rack, a communication for example taking place by means of the rack. Just as well, infusion stations may be standalone pump devices which by themselves are connected to a hospital communication network.

By a setup of the kind described herein a communication infusion stations having pump devices of one or multiple different manufacturers and front-end-computing devices may be enabled, the pump devices belonging to different families and having different types and using different communication channels defined by different protocols.

LIST OF REFERENCE NUMERALS

1 Infusion station
10 Rack
11 Medical device
12 Infusion station (medical device)
2 Front-end computing device
3 Server system
4 Communication network
A1 Upstream direction
A2 Downstream direction
C1-C4 Communication channel
d1-d5 Extracted data
D1, D2 Device type
DP1-DP4 Driver module
F1, F2 Device family
M Data model
M1, M10-M19 Data structure
M180-M182 Data structure
M190-202 Data structure
m1-m3 Message
P1-P4 Protocol
VD Virtual device protocol
VD1, VD2 Virtual device
U User

The invention claimed is:

1. A method for data communication between at least one infusion station and at least one front-end computing device in a healthcare environment, comprising:
    at least one of in an upstream direction transmitting and in a downstream direction receiving data, by the at least one infusion station for carrying out an infusion operation, and
    at least one of in the upstream direction receiving and in the downstream direction transmitting data relating to the at least one infusion station by the at least one front-end computing device,
    at least one of in the upstream direction receiving data from and in the downstream direction transmitting data to the at least one infusion station by a driver module, and
    at least one of in the upstream direction transmitting data to and in the downstream direction receiving data from the at least one front-end computing device by a virtual device module,
    wherein the driver module at least one of, in the upstream direction, processes data received from the at least one infusion station to provide said data to the virtual device module and, in the downstream direction, processes data received from the virtual device module to transmit said data to the at least one infusion station,
    wherein the virtual device module includes a data model defining a plurality of data structures in which data relating to the at least one infusion station is stored during transfer of the data between the at least one infusion station and the at least one front-end computing device, the plurality of data structures being independent from communication protocols by which the data is communicated in between the at least one infusion station and the driver module.

2. The method according to claim 1, wherein the at least one infusion station uses a first communication protocol for communicating with the driver module.

3. The method according to claim 2, wherein different driver modules communicate with different infusion stations using different first communication protocols.

4. The method according to claim 2, wherein the first communication protocol is based on HTTP, MQTT or Ethernet.

5. The method according to claim 2, wherein the virtual device module uses a second communication protocol for communicating with the at least one front-end computing device.

6. The method according to claim 5, wherein the second communication protocol is based on AMQP or HTTP.

7. The method according to claim 2, wherein the virtual device module, as a second communication protocol, uses an upstream protocol in the upstream direction and a downstream protocol different than the upstream protocol in the downstream direction.

8. The method according to claim 7, wherein the upstream protocol is based on AMQP.

9. The method according to claim 7, wherein the downstream protocol is based on HTTP.

10. The method according to claim 1, wherein the virtual device module stores data received from the at least one infusion station or from the at least one front-end computing device in predefined data structures of the data model.

11. The method according to claim 1, wherein the virtual device module stores data relating to at least one of an identity of a pump device of an infusion station, a status of a pump device of an infusion station, and a capability of a pump device of an infusion station in predefined data structures of the data model.

12. The method according to claim 1, wherein the driver module is implemented as a dynamic-link library or windows services.

13. The method according to claim 1, wherein the virtual device module groups pump devices of infusion stations belonging to a common device family.

14. The method according to claim 1, wherein different virtual device modules group pump devices belonging to different device families.

15. A system for data communication in a healthcare environment, comprising:
- at least one infusion station for carrying out an infusion operation, the at least one infusion station being configured to at least one of in an upstream direction transmit and in a downstream direction receive data,
- at least one front-end computing device being configured to at least one of in the upstream direction receive and in the downstream direction transmit data relating to the at least one infusion station, and
- a server system hosting a driver module and a virtual device module,
- the driver module being configured to at least one of in the upstream direction receive data from and in the downstream direction transmit data to the at least one infusion station, and
- the virtual device module being configured to at least one of in the upstream direction transmit data to and in the downstream direction receive data from the at least one front-end computing device,
- wherein the driver module is configured to at least one of, in the upstream direction, process data received from the at least one infusion station to provide said data to the virtual device module and, in the downstream direction, process data received from the virtual device module to transmit said data to the at least one infusion station,
- wherein the virtual device module includes a data model defining a plurality of data structures in which data relating to the at least one infusion station is stored during transfer of the data between the at least one infusion station and the at least one front-end computing device, the plurality of data structures being independent from communication protocols by which the data is communicated in between the at least one infusion station and the driver module.

* * * * *